United States Patent [19]

Hata

[11] Patent Number: 4,521,515

[45] Date of Patent: Jun. 4, 1985

[54] BACTERIAL STRAIN FOR PURIFYING HYDROCARBONS POLLUTION AND PURIFICATION PROCESS

[75] Inventor: Kosei Hata, Osaka, Japan

[73] Assignee: Seiken Kai Foundation Juridical Person, Japan

[21] Appl. No.: 313,405

[22] Filed: Oct. 21, 1981

[51] Int. Cl.³ .................. C12N 1/26; C12N 1/20; C12N 1/36; C12N 15/00; C10G 32/00; C12R 1/38

[52] U.S. Cl. .................. 435/248; 435/253; 435/245; 435/172.1; 435/281; 435/802; 435/874; 210/611; 210/922

[58] Field of Search ........... 435/172, 248, 249, 250, 435/253, 264, 281, 802, 874, 262, 245, 172.1; 210/611, 922

[56] References Cited

U.S. PATENT DOCUMENTS

| | | | |
|---|---|---|---|
| 3,620,927 | 6/1971 | Leathen | 435/253 |
| 3,721,604 | 3/1973 | Silver et al. | 435/802 |
| 3,769,164 | 10/1973 | Azarowicz | 435/281 |
| 3,813,316 | 5/1974 | Chakrabarty | 435/172 |
| 3,871,957 | 3/1975 | Mohan et al. | 435/281 |
| 3,941,692 | 3/1976 | Gutnick et al. | 210/922 |
| 4,042,495 | 8/1977 | Marconi et al. | 435/281 |
| 4,259,444 | 3/1981 | Chakrabarty | 435/253 |

OTHER PUBLICATIONS

Davis, "Petroleum Microbiology", Elsevier Publishing Company, N.Y. (1967) pp. 216–221, 229, and 350–353.

Primary Examiner—Lionel M. Shapiro
Assistant Examiner—John E. Tarcza
Attorney, Agent, or Firm—Sughrue, Mion, Zinn, Macpeak, and Seas

[57] ABSTRACT

A bacterial strain comprising a strain of Pseudomonas exhibits acceleration of growth in a logarithmic phase in a trophic culture medium when hydrocarbons are added thereto, a process for producing such a bacterial strain, and a purification process using such a bacterial strain.

16 Claims, 6 Drawing Figures

CULTURE MEDIUM: BRINE + 30ppm CRUDE OIL (a) E.coli
(b) PSEUDOMONAS
(c) LACTOBACILLAS

BACTERIAL STRAIN FOR PURIFYING HYDROCARBONS POLLUTION AND PURIFICATION PROCESS

FIELD OF THE INVENTION

The present invention relates to the utilization of Pseudomonas which rapidly carry out assimilation, growth and emulsification in an oligotrophic environment of brine and hydrocarbon and rapidly perishes after assimilation. The Pseudomonas used in the present invention has the characteristic that it multiplies in a short period to emulsify and assimilate hydrocarbons and rapidly perishes within the period required for multiplication thereof, which is opposed to common bacteriological expectations.

The present invention also relates to an agent comprising said bacteria which utilizes the characteristics of the bacteria and to a method of using the same.

Well known bacteria rapidly multiply with good nutrition in an acceptable environment, particularly, in the logarithmic phase.

Typically, when petroleum is added during the bacterial logarithmic growth phase, the multiplication rate thereof rapidly deteriorates in a short time in spite of bacteria cultured on the good nutrient, because petroleum is toxic thereto. The present invention, however, relates to the development and practical application of bacteria which exhibit acceleration of growth when hydrocarbon, which should be toxic by nature in a culture medium therefor, is added thereto.

BACKGROUND OF THE INVENTION

Marine pollution due to hydrocarbons, especially petroleum products has been analyzed in detail with respect to the amount of petroleum introduced due to accidents, the direction of petroleum flow, the state of dispersion thereof, decomposition and scattering effects due to flowing petroleum on the sea, shoreline pollution and the like.

Further, microbial decomposition oil has also been reported. For example, one theory postulates that in the case of petroleum spread on the surface of the sea as a "membrane" 0.1–0.4μ thick, components which do not volatilize are attacked by various microbes within 1–2 weeks so that a considerable part of the petroleum is decomposed within 2–3 months. Further, it has been reported that the amount of decomposition due to other organisms or due to spontaneous oxidation is about 1/10 that due to microbes.

At present, there is a rapid growth of knowledge concerning petroleum and its effects on the marine environment and organisms having a relationship therewith one detailed report is "Collective investigation for environmental influence concerning matter of oil flowing in Mizushima" issued by the Environment Agency of Japan on March 12, 1977. Per this report, oil introduced into the sea seems to be substantially decomposed or dispersed after 1 year. However, per oil pollution investigations by the International Oceanography Committee (IOC) of the United Nations Educational, Scientific, and Cultural Organization (UNESCO) and the World Meteorological Organization (WMO) during 1975–1979, it appears that marine oil pollution results in serious problems which cannot be reconciled with the theory that almost all oils are assimilated by microbes without the passage of long periods of time. In fact, it was recently reported that many oil tankers had serious problems arising from washing the holds of supertankers and throwing sludges away and others relating to oil tankers, which created an abrupt realization of this type of problem with those concerned with marine pollution and, led to a discussion of such problems by governmental bodies. Further, the fact that treatment of oils having a low concentration drifted near to shore is very difficult to carry out has become an issue.

The act is aware of processes for separating petroleum decomposing microbes or petroleum component decomposing microbes such can roughly be classified into two methods. One uses a culture medium composed of inorganic marine salts, $NH_3$ salts (or urea) and petroleum or petroleum components; the other uses a culture medium prepared by adding an eutrophic material such as a vitamin, Casamino acid or a yeast extract to the above described culture medium. It is known that in the case of multiplying oxidative microbes complex having activity in a high nutrition condition such as in the latter method the culture medium becomes cloudy by shaking cultivation at 20° C. for 10 days.

SUMMARY OF THE INVENTION

After extensive studies regarding marine petroleum pollution, the present inventors completed the present invention.

Specifically, the present invention provide an agent which comprises a strain of Pseudomonas incubated with a trophic culture medium which exhibits an acceleration of growth when a hydrocarbon(s) is/are added thereto, and provides a process for purifying a polluted area which comprises multiplying a strain of Pseudomonas incubated with a trophic culture medium which exhibits acceleration of growth when a hydrocarbon(s) is/are added thereto.

DETAILED DESCRIPTION OF THE INVENTION

It is known from Japanese Patent Applications (OPI) Nos. 61376/74 and 142865/76 that one can purify brine polluted with petroleum with utilizing bacteria which decompose and assimilate petroleum hydrocarbons. (The term OPI as used herein refers to a "published unexamined Japanese Patent application", hereafter the same).

In the former Application a unicellular microbe containing a first energy generating plasmid defining a decomposition path and a unicellular microbe containing at least one energy generating plasmid which cannot coexist with the first plasmid are selected as a donor microbe and a recipient microbe, respectively, and conjugation of the donor microbe and recipient microbe is effected. In order to stabilize the resultant unstable supermicrobe and obtain a new microbe having desired characteristics, experimentation was carried out to develop a unicellular microbe having the ability of decomposing and assimilating hydrocarbon compounds, particularly to control organisms by utilizing genetics for marine petroleum pollution using single species of Pseudomonas. Thus, a single microbe capable of decomposing all linear aliphatic-, cycloaliphatic-, aromatic- and polynuclear aromatic hydrocarbons was obtained.

In distinction, the latter Application was based on the discovery that 1000 ppm of heavy oil components could be removed within 5 days, to the stage that heavy oil components remain as only a trace upon thin layer chromatography, by multiplying a single microbe in a culture medium composed of inorganic materials and heavy oil components.

However, in both of these Applications the microbe multiplying is carried out in the presence of an added nitrogen tophic source, i.e., in the presence of $NH_3$ in the former and $NH_2CONH_2$ in the latter, whereby the crude petroleum or heavy oil is decomposed and assimilated in an eutrophic culture medium. It can be seen that these Applications use microbes which grow in an environment remarkably different from the sea pollution by petroleum. In the former, a culture medium which does not contain salts present in high amount in the sea (such as NaCl) but which contains 2.1 g/l of $NH_3$ and 10 mg/l of vitamin C is used. In the latter, a culture medium containing 0.25 g/l of $NH_2CONH_2$ is used. These culture media are eutrophic culture media as opposed to sea polluted by petroleum which consists of petroleum and brine.

Figure 5:
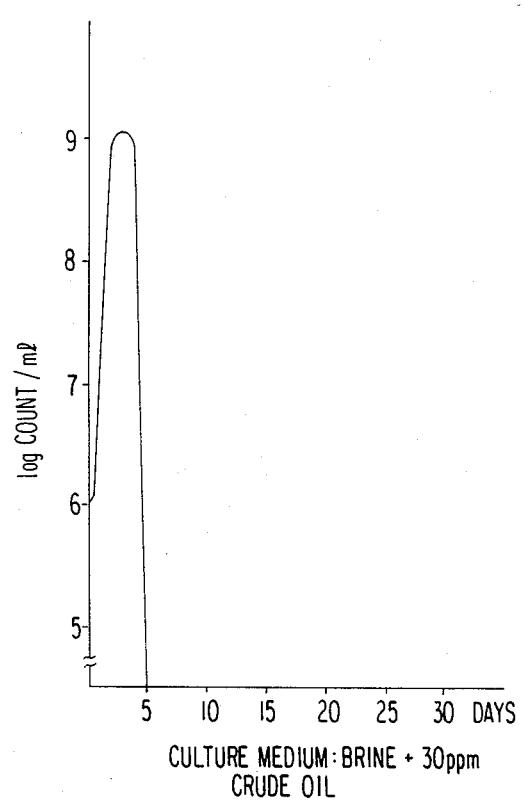
FIG. 5 is a curve to show multiplication and death of the strain according to the present invention.
Figure 6:
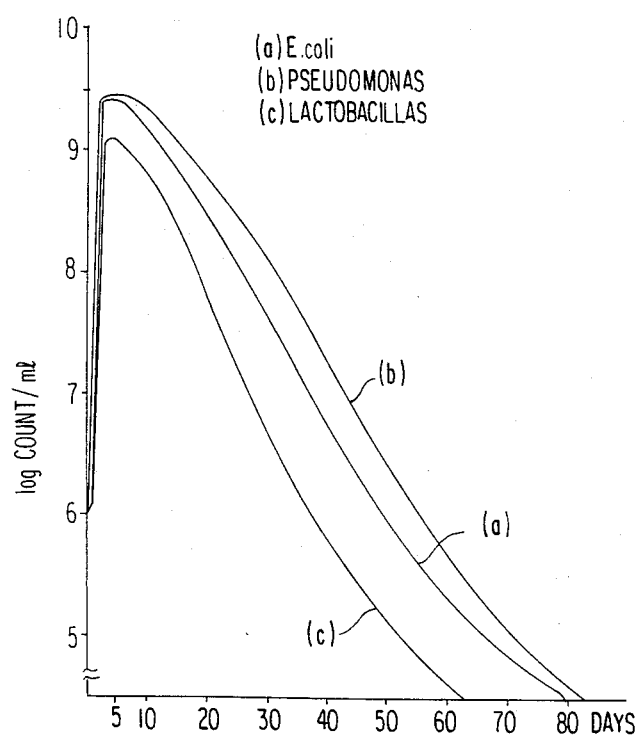
FIG. 6 is a curve to show multiplication and death of the well known strains.

The Pseudomonas according to the present invention has characteristics quite different from those of the microbes in the above described Applications. Specifically: (1) it assimilates hydrocarbons under oligotrophic conditions of only brine and hydrocarbons at a temperature varying over a wide range in a culture medium having an hydrocarbon content varying over a wide range, at a very good consumption rate; and (2) rapid multiplication and emulsification occur after inoculation of the bacteria and it rapidly perishes after conclusion of assimilation of crude petroleum. Particularly, the time from multiplication to death is far less than reasonable expectation, i.e. The period required for multiplication is nearly equal to the period from conclusion of multiplication to death. Speaking more specifically, the period required for multiplication is about 1.5 days, the stationary period is about 0.5 days and the period therefrom to death is about 2.5 days in the case of a crude oil content of 30 ppm; and the period required for multiplication is about 2.5 days, the stationary period is about 1 day and the period till death is about 4 days in the case of a crude oil content of 500 ppm. FIG. 5 shows a curve of multiplication and death of bacteria of the present invention having an assimilating ability to 30 ppm of crude oil. FIG. 6 shows the same of well known bacteria. As is apparent from the Figures, in the case of the bacteria of the present invention, time from multiplication to death is very short.

The Pseudomonas according to the present invention is thus seen to be a bacteria which exhibits growth acceleration in the presence of hydrocarbons.

Bacteria belonging to the genus Pseudomonas presently used in this invention are widely diverse with no relationship to the classification of the bacteria as the growth acceleration ability of the present bacteria by petroleum hydrocarbon does not depend on the classification of the bacteria. However, the Pseudomonas of the present invention preferably include putida, aureofaciens, stutzeri, oleovorans, arctica, oceanica, calcis, rubescens, cichorii, propanica, elongata, mendocina, citronellolis, pictorum, marginata, facilis, saccharophila, obscura, aromatica, acidovorans, sessilis, rathonis, cruciviae, arvilla, palleronii, etc., most preferably Ferm (Deposition number Fermentation Research Institute) BP-63 and 64.

The Pseudomonas according to the present invention has a growth stimulation angle of at least 1°, preferably more than 1.5° and EP value of at least 0.1, preferably more than 0.3, as later defined.

One primary characteristic of the bacteria used herein lies in the fact that the bacteria perishes rapidly when the amount of hydrocarbon is less than 0.1 ppm. Thus, the microbe does not increase nor remain after completion of purification of hydrocarbon pollution. The temperature at which the bacteria is active ranges from $-5°$ C. to 50° C.

The bacteria of the present invention has the ability to purify 0.1 ppm to 3,000 ppm, preferably 10 ppm to 2,000 ppm, of hydrocarbons. The hydrocarbons removed by the present bacteria include natural gas, petroleum, liquefied coal, hydrocarbons contained therein, such as paraffinic hydrocarbon, e.g. a pentane, a hexane, etc., a naphthenic hydrocarbon, e.g., a cyclopentane, a cycloheptane, etc., an aromatic hydrocarbon, e.g., a benzene, a toluene, a naphthalene, a tetrabutyl benzene, etc. and petroleum products, such as gasoline, kerosene, light-oil, heavy oil, etc.

The Pseudomonas according to the present invention can be obtained from Pseudomonas in the brine, preferably Pseudomonas separated from brine as is described in Japanese Patent Application (OPI) No. 142865/76.

The process for producing the Pseudomonas of the present invention comprises;

(1) Culturing the Pseudomonas in the brine, preferably Pseudomonas obtained from the brine according to the procedures of the above Japanese Patent Application (OPI) No. 142865/76, on a medium comprising brine, one or more hydrocarbons and a trophic source containing at least one nitrogen compound. The medium comprises 0.1 g to 10 g of hydrocarbon and 0.01 g to 1 g of nitrogen compound per 1,000 ml of brine. When the culture medium becomes faintly opaque, a small quantity of the culture medium is inoculated on an above described medium comprising brine, hydrocarbons and a trophic source. The operation is repeated 20 to 60 times, preferably 30 to 50 times, but the addition amount of the trophic source is gradually reduced whereby the bacteria become capable of growing and multiplying without the trophic source. The time when the bacteria became capable of growing and multiplying without the trophic is determined based on an appearance of a faint cloudiness. When the culture medium becomes cloudy within 15 hours after addition of the picked up medium containing bacteria without the trophic source the cultivation of step (1) is completed.

(2) Culturing the bacteria obtained in above step (1) on a medium comprising brine, one or more hydrocarbons and vitamins. The medium comprises 0.001 g to 0.1 g of vitamine and 0.001 g to 10 g preferably 0.01 g to 20 g of hydrocarbon per 1,000 ml of brine. The same operations as is described in step (1) are repeated except for using vitamins instead of the trophic source. The above operation is repeated 40 to 100 times, preferably 50 to 90 times.

(3) Culturing the bacteria obtained in above step (2) on a medium of brine sol containing of agar and a paper disc thereon, which is permeated by 0.15 mg to 0.6 mg of hydrocarbons per 1 cm$^3$ of paper disc. After cultivation, the bacteria are fished from the most outside of the colony a from the raised part of the colony, and cultivated on a medium comprising brine and 0.001 g to 10 g preferably 0.01 g to 2.0 g of hydrocarbons per 1,000 ml of brine. During cultivation, radiation may be applied in an amount of 1 to 3 mr/sec., 1 to 20 hours.

The above operation is repeated 25 to 85 times, preferably 35 to 75 times, until the whole culture medium comprising brine and hydrocarbons is emulsified within 15 hours after inoculation on the culture medium.

In above steps (1) and (2), the hydrocarbon(s) used as one component of the medium is preferably A-heavy oil, gasoline, light-oil, kerosene, crude oil of high quality having lower distillating temperature, etc. The petroleum hydrocarbon(s) used in step (3) is preferably one having a higher quality having lower distillating temperature such as light-oil, gasoline, A-heavy oil, etc., at initial subculturing steps and one of lower quality having higher distillating temperature, such as C-heavy oil, B-heavy oil, etc., at final subculturing steps. A-heavy oil, B-heavy oil and C-heavy oil has not more than 20 cm$^2$/sec, 50 to 150 cm$^2$/sec and 50 to 400 cm$^2$/sec of kinematic viscosity, respectively. Other characteristics regarding A-, B- and C-heavy oil is described in the Japan Industrial Standard (JIS) No. K2205-1958.

The brine used in the above steps is collected from brine near a fishing port, as an embodiment, from brine near Sakai fishing port in Osaka bay.

The nitrogen compound(s) used in the step (1) includes compounds having $NH_2$—, $NH_4^+$ or $NO_3^-$, such as $KNO_3$, $NaNO_3$, $NH_4Cl$, $(NH_4)_2HPO_4$, $(NH_4)H_2PO_4$, $(NH_4)_2SO_4$, $NH_2CONH_2$, etc., and is added in an amount of 0.001 to 5 g, preferably 0.01 to 2 g per 1 l of the brine.

In step (1), vitamins, starch such as starch from grain, e.g., corn, potato, wheat, etc. may be added to the medium in an amount of 1% to 100%, preferably 1% to 30% by weight of the amount of nitrogen compound(s).

The vitamins used in step (2) and step (1) include those other than vitamin P, preferably folic acid, nicotinamide Vitamins $B_1$, $B_{12}$, $B_6$ and C, pantothenic acid, biotin, etc., and mixture thereof, more preferably Vitamin $B_6$, folic acid nicotinamide, in an amount of more than 0.00005 mg, preferably 0.0005 mg to 100 mg, most preferably 0.001 mg to 5 mg per 1 l of the brine.

The culturing temperature is $-5°$ C. to $50°$ C., preferably $10°$ C. to $40°$ C., and cultivation is applied at an ambient pressure, in steps (1) to (3).

In addition to the above steps (1) to (3), steps (4) and (5) hereinafter described may also follow. In step (4), bacteria are acclimatized to a higher concentration of hydrocarbons, that is, the bacteria obtained in step (3) are cultivated on a medium containing brine and higher concentration of hydrocarbons. Thus, the cultivation is repeated until the bacteria have a desired assimilating ability to a higher concentration of hydrocarbons, that is, until the whole culture medium is emulsified within 15 hours after inoculation on the medium. Generally, the cultivation is operated 70 to 100 times.

In step (5), bacteria are acclimatized to a wide range of temperature, that is, the bacteria obtained in step (3) are cultivated on a medium comprising brine and hydrocarbons under more higher or lower temperature and thus the cultivation is repeated so the bacteria exhibit an assimilating ability to a desired temperature ranged from low temperature to high temperature, $-5°$ C. to $50°$ C. The cultivation is repeated 70 to 100 times. When the whole culture medium is emulsified within 15 hours after inoculation, the acclimation is completed.

The culturing temperature in step (4) is $-5°$ C. to $50°$ C., preferably $10°$ C. to $40°$ C. In steps (4) and (5), cultivation is applied at an ambient pressure, and the medium used in steps (4) and (5) is the same as that used in the above step (3). In order, step (5) may precede step (4) or vice versa.

Step (1)

Ferm (Deposition number in Fermentation Research Institute) P-2927 and 2928 were used as bacteria; they were inoculated on a culture medium having the following composition to effect cultivation.

| Composition of culture medium | |
|---|---|
| Brine | 1000 ml |
| A-heavy oil | 1 g |
| $(NH_4)_2SO_4$ | 0.5 g |
| Starch (Potato) | 0.2 g |
| Vitamin | 0.01 g |
| Cultivation temperature | 18° C. |

*Vitamin contains 4500 I.C. of Vitamin A, 7.2 mg of Vitamin $B_1$, 5.6 mg of Vitamin $B_2$, 5.6 mg of Vitamin $B_6$, 0.000025 g of Vitamin $B_{12}$, 80 mg of nicotinamide, 40 mg of calcium pantothenate, 320 mg of vitamin C and 600 I.C. of Vitamin D.

When the culture medium became opaque, a part of the culture medium was inoculated on a new medium containing the same components as described above. The operation was repeated 30 times wherein addition of the $(NH_4)_2SO_4$ was gradually reduced, whereby the bacteria became capable of growing and multiplying with only the brine and A-heavy oil, i.e., without adding any trophic material(s).

Step (2)

The bacteria obtained in step (1) were used; they were inoculated on a culture medium having the following composition to carry out cultivation.

| Composition of culture medium | |
|---|---|
| Brine | 1000 ml |
| Crude petroleum | 30 ppm |
| Vitamin | 0.01 g/l |
| Cultivation temperature | 21° C. |

*Vitamin used in step (2) is the same as used in step (1).
**Crude petroleum comprises Khufuji crude oil and has following physical properties; specific gravity: 0.885, pour point $-35°$ C., viscosity: 60.4 R.W., sulfur content; 3.1 wt %, nitrogen content: 0.25 wt %, carbon residue: 8.0 wt % and wax content: 2.9 wt %.

When cultivation was carried out at 21° C. on the above described culture medium, bacteria which caused cloudiness were obtained after 10-15 days. The cloudy medium was inoculated on a new culture medium containint the same components as above described. Thus, the operation was repeated 70 times while gradually decreasing the Vitamin content, whereby bacteria having sufficiently multiplying with the medium containing only the brine and crude petroleum were obtained (residual amount of petroleum 4 ppm).

Step (3)

The bacteria obtained in the step (2) were inoculated on a medium of brine sol containing 1.5 wt.% of agar and a paper disc thereon which is permeated by 0.4 mg of crude petroleum per 1 cm$^3$ of paper disc. After cultivation, the bacteria are fished from the raised part of the colony and inoculated on a medium comprising brine and 30 ppm of hydrocarbons. The operations were repeated 55 times. Thus, bacteria having the ability of complete assimilation of 30 ppm petroleum within only 1.5 days were obtained. Specifically, these bacteria show high activity in the presence of crude petroleum but they undergo autolysis to rapidly perish if the crude petroleum is absent. Further, these bacteria perished within nearly the same period as this multiplication period under oligotropic conditions in the precence of only brine and crude petroleum. This phenomenon was discovered by the present inventors and was not suspected by the prior art, though it was known in the art that bacterial death is caused by bacteriolysis by bacteriophage or antibiotics.

Step (4)

Acclimation of the bacteria obtained in step (3) was repeated till the bacteria had the highest assimilation ability with respect to a crude petroleum concentration ranging from an amount solubility in the sea (30 ppm) to an amount floating on the surface of the sea (1500 ppm). First, the bacteria were inoculated at a low concentration (30 ppm) of crude petroleum, emulsification of the Petroleum resulted after 4–5 hours. After confirmation of complete emulsification of petroleum by the bacteria, the concentration of the crude petroleum was gradually increased. Bacteria which multiplied well in desired crude petroleum concentrations, 30 ppm, 100 ppm, 300 ppm, 500 ppm and 1000 ppm were obtained. The confirmation that the above acclimated bacteria were obtained is carried out by a recognition of complete emulsification within 15 hours after inoculation under each 30 ppm, 100 ppm, 300 ppm, 500 ppm and 1000 ppm of hydrocarbons in brine. When the resultant bacteria were used, complete assimilation could be obtained within 1.5 days in case of a crude petroleum concentration of 30 ppm using bacteria assimilated by 30 ppm petroleum, i.e., 30 ppm acclimation bacteria, 2 days in the case of 300 ppm using 300 ppm acclimation bacteria, 2.5 days in case of 500 ppm using 500 acclimation bacteria and about 3 days in the case of 1000 ppm, using 100 ppm of acclimation bacteria.

Step (5)

The resultant bacteria were then subjected to acclimation so they would be effective at high temperature (for example 37° C.) and at low temperature (about 8° C.) by 25 repeated operations at a temperature higher than or lower than their optimum multiplication temperature (18°–30° C.) so as to not deteriorate the functions of multiplication, emulsification and assimilation of the bacteria. Thus, the bacteria were acclimated till this activity at high temperature (37°) was 115 and at a low temperature (8° C.) was 50 based on this activity at this optimum multiplication temperature being 100. For example, bacteria capable of complete assimilation of 30 ppm of the crude petroleum within 1.5 days at optimum temperature and a high temperature and 3 days at a low temperature could be obtained.

In removing petroleum pollution, the bacteria or a bacterial preparation derived from the bacteria of the present invention is used in the presence of the brine. The amount of brine is 100 to 1,000,000 parts by weight per 1 part by weight of the petroleum to be removed, and the amount of the bacteria is 1/1,000 to 1/5,000,000 parts by weight per 1 part by weight of brine.

In the purifying process of the present invention, the removal ratio of petroleum is at least 70%, and is generally more than 90%. After purification, the bacteria rapidly perish, suitable temperatures for purification are −5° C. to 50° C.

The bacterial preparation can be obtained by a process which comprises subjecting a medium containing bacteria thus obtained to centrifugal separation at 5000× g to 1200× g to form a mixture of the bacteria and a hydrocarbon emulsion, mixing a coating agent with the mixture thus obtained and drying, preferably drying by vacuum lophilization. The dried material thus obtained may be affected by inert atmosphere, such as an atmosphere without $O_2$, an atmosphere with $CO_2$, $N_2$, helium, neon, etc. The coating agent used in the present invention includes starch, sulfur-containing amino acids such as cystein, crude oil, glutamic acid, vitamins, A-heavy oil, B-heavy oil, C-heavy oil, etc. The starch, vitamins, and A-, B- and C-heavy oil are those defined previously. The amount of the coating agent used is 1 to 500 wt%, preferably 10 to 100 wt% to the weight of the bacteria.

The preparation is preferably preserved under refrigerated conditions to increase the preservation period, preferably 0° C. to 10° C. Further, it is more preferable for preservation of the preparation to produce the bacterial preparation under the condition wherein $O_2$ is excluded, to lower the moisture content in the preparation by drying and/or to coat the preparation by coating agent.

The resultant bacteria have the novel characteristics that bacteria assimilate hydrocarbons in the sea in the presence of hydrocarbons without adding any other materials and show a hydrocarbon removal ratio of 99.5% or higher, but such bacteria rapidly die when the petroleum is gone.

The resultant bacteria have remarkably high practical value for removing polluting hydrocarbons from the viewpoint of safety, since this assimilation ability rapidly deteriorates in an environment where petroleum is not existent and the same change into this original bacterial form or they rapidly die in the presence of only brine.

Furthermore, it was confirmed that the living bacteria and cultivation supernatant of the bacteria are safe, by carrying out prescribed tests regarding there acute, subacute and chronic properties. Further, no abnormality was observed when food containing the living bacteria was orally administered to mice and a large amount of bacteria was applied to the eyes of mice.

Figure 1:
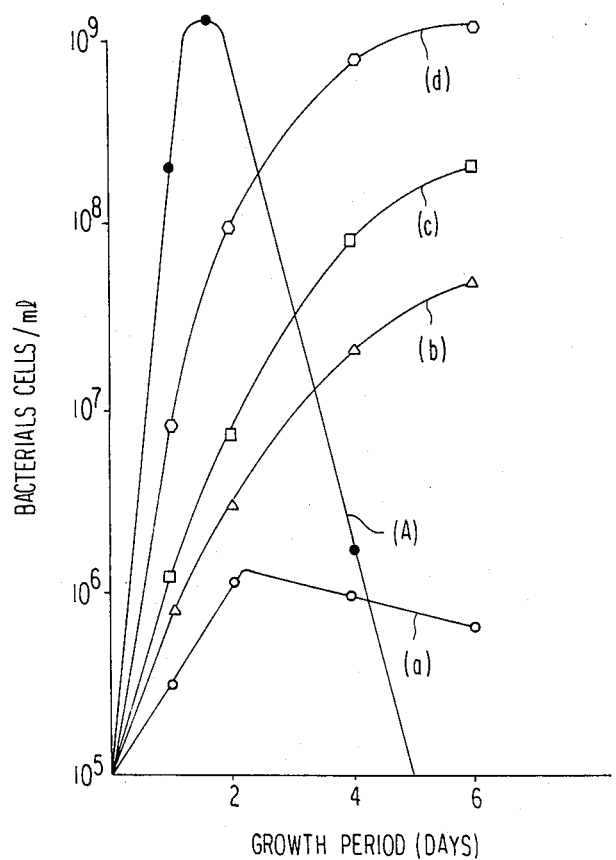
FIG. 1 is a growth curve of the strain according to the present invention.

FIG. 1 shows one characteristic of the bacteria according to the present invention, from which it can be understood that the characteristic of the bacteria according to the present invention is remarkably different from that of known bacteria. Namely, growth curve (A) of the bacteria of the invention in a culture medium containing 30 ppm of crude petroleum to brine shows a rapid ascent and a rapid descent, while growth curves (a)–(d) of the microbes described in Japanese Patent Application (OPI) No. 61376/74 are as shown in the drawing. With microbes as described in the above Patent Application, the viable cell count is still $10^9$ in the case of adding 50,000 ppm of petroleum. This means that the microbes reach a stationary phase by passing through a logarithmic phase. In distinction, with the bacteria of the present invention a cell yield of 35 hundred million is shown even in the case of adding only 500 ppm of petroleum, and the time of reaching such a cell yield is very short, i.e., at resembles. The growth multiplication rate in the case of incubating colon bacteria having a high growth rate in an eutrophic culture medium. Further, the growth environment in the above Patent Application is eutrophic, whereas that in the present invention is oligotrophic and consists only or the brine and crude petroleum. Thus, the rapid ascent in the growth curve of the bacteria according to the present invention is due to the growth acceleration effect of the petroleum on the bacteria, a characteristic not shown in prior microbes.

The most important characteristic of the bacteria according to the present invention will now be illustrated in greater detail.

When the bacteria grown by the above described six steps are subjected to repeated operation on a Stephenson Whetham culture medium having the later described composition, (1) the degree of growth acceleration upon addition of crude petroleum, (2) emulsification ability and (3) assimilation ability deteriorate with increased numbers of operating generations. On the basis of this phenomenon, it is seen that characteristics of the bacteria are closely related to rapid multiplication and rapid death under the oligotrophic conditions which are characteristics required for removing polluting petroleum or nearly complete consumption, thereof.

The Stephenson Whetham, culture medium (hereafter referred to as a S-W culture medium) has the following composition: $KH_2PO_4$ 1 g; $MgSO_4 \cdot 7H_2O$ 0.7 g; NaCl 1 g; $(NH_4)_2HPO_4$ 4 g; glucose 5 g and $FeSO_4 \cdot 7H_2O$ 0.03 g, per 1 liter of water (compositions of culture media are per 1 liter of water, hereafter).

(1) Retrogression of growth acceleration with increased operating generations in (S-W) culture medium (a) Bacteria acclimated by 500 ppm of crude petroleum.

Strains each having a different operating generation were incubated on the (S-W) culture medium and the degree of growth acceleration of these strains was observed by measuring turbidity of the culture medium containing strains was when added 10 ppm, 30 ppm, 100 ppm, 300 ppm and 500 ppm of crude petroleum in the logarithmic growth phase thereof. Turbidities as the results of measurement are shown in Table 1. In the measurement, petroleum was extracted with hexane and turbidity is measured with UV (460 nm).

One generation means a period from fishing, when strains show the maximum growth speed, to inoculation and culturing on a new-culturing medium.

TABLE 1

| Amount added | Elapsed time after addition of crude petroleum (minutes) | | | | | | | |
|---|---|---|---|---|---|---|---|---|
| | 0 | 20 | 40 | 60 | 90 | 120 | 180 | 240 |
| 1st generation | | | | | | | | |
| Comparative sample* | 50 | 51 | 52 | 53 | 55 | 57 | 60 | 65 |
| 10 ppm | 50 | 51 | 52 | 53 | 55 | 58 | 61.5 | 67 |
| 30 ppm | 50 | 51 | 52 | 53 | 55 | 59 | 62 | 68 |
| 100 ppm | 50 | 51 | 52 | 53 | 55 | 59.5 | 62.5 | 68.5 |
| 300 ppm | 50 | 51 | 52 | 53 | 55 | 59.5 | 62.5 | 68.5 |
| 500 ppm | 50 | 51 | 52 | 53 | 55 | 59.5 | 62.5 | 68.5 |
| 4th generation | | | | | | | | |
| Comparative sample | 50 | 51 | 52 | 53.5 | 56 | 58.5 | 62 | 67 |
| 10 ppm | 50 | 51 | 52 | 53.5 | 56 | 58.5 | 62.5 | 57.5 |
| 30 ppm | 50 | 51 | 52 | 53.5 | 56 | 59 | 63 | 68.5 |
| 100 ppm | 50 | 51 | 52 | 53.5 | 56 | 59.5 | 64 | 69 |
| 300 ppm | 50 | 51 | 52 | 53.5 | 56 | 59.5 | 64 | 69 |
| 500 ppm | 50 | 51 | 52 | 53.5 | 56 | 59.5 | 64 | 69 |
| 6th generation | | | | | | | | |
| Comparative sample | 50 | 51 | 52 | 53.5 | 56 | 58.5 | 62 | 67 |
| 10 ppm | 50 | 51 | 52 | 53.5 | 56 | 58.5 | 62 | 67 |
| 30 ppm | 50 | 51 | 52 | 53.5 | 56 | 58.5 | 62.5 | 68 |
| 100 ppm | 50 | 51 | 52 | 53.5 | 56 | 58.5 | 62.5 | 68 |
| 300 ppm | 50 | 51 | 52 | 53.5 | 56 | 58.5 | 62.5 | 68 |
| 500 ppm | 50 | 51 | 52 | 53.5 | 56 | 58.5 | 62.5 | 68 |
| 8th generation | | | | | | | | |
| Comparative sample | 50 | 51 | 52 | 53.5 | 56 | 58.5 | 62 | 67 |
| 10 ppm | 50 | 51 | 52 | 53.5 | 56 | 58.5 | 62 | 67 |
| 30 ppm | 50 | 51 | 52 | 53.5 | 56 | 58.5 | 62 | 67 |
| 100 ppm | 50 | 51 | 52 | 53.5 | 56 | 58.5 | 62.5 | 67.5 |
| 300 ppm | 50 | 51 | 52 | 53.5 | 56 | 58.5 | 62.5 | 67.5 |
| 500 ppm | 50 | 51 | 52 | 53.5 | 56 | 58.5 | 62.5 | 67.5 |
| 10th generation | | | | | | | | |
| Comparative sample | 50 | 51 | 52 | 53.5 | 56 | 58.5 | 62 | 67 |
| 10 ppm | 50 | 51 | 52 | 53.5 | 56 | 58.5 | 62 | 67 |
| 30 ppm | 50 | 51 | 52 | 53.5 | 56 | 58.5 | 62 | 67 |
| 100 ppm | 50 | 51 | 52 | 53.5 | 56 | 58.5 | 62 | 67 |
| 300 ppm | 50 | 51 | 52 | 53.5 | 56 | 58.5 | 62.5 | 67 |
| 500 ppm | 50 | 51 | 52 | 53.5 | 56 | 58.5 | 62 | 67 |
| 12th generation | | | | | | | | |
| Comparative sample | 50 | 51 | 52 | 53.5 | 56 | 58.5 | 62 | 67 |
| 10 ppm | 50 | 51 | 52 | 53.5 | 56 | 58.5 | 62 | 67 |
| 30 ppm | 50 | 51 | 52 | 53.5 | 56 | 58.5 | 62 | 67 |
| 100 ppm | 50 | 51 | 52 | 53.5 | 56 | 58.5 | 62 | 67 |
| 300 ppm | 50 | 51 | 52 | 53.5 | 56 | 58.5 | 62 | 67 |
| 500 ppm | 50 | 51 | 52 | 53.5 | 56 | 58.5 | 62 | 66.5 |

*No addition of crude petroleum; the same hereinafter

It can be understood from the Table 1 that:

(1) Strains of the 1st generation operating on the (S-W) culture medium—which are hardly weakened—are undergo high growth acceleration 120 minutes from the addition of the crude petroleum and the degree of growth acceleration increases with increasing amounts of petroleum added (cases of adding more than 100 ppm show the same results as that in case of adding 100 ppm). (Refer to numerical values underlined in the Tables).

(2) Strains of the 4th generation operating on the (S-W) culture medium which are somewhat weakened are subject to growth acceleration 180 minutes from petroleum addition. In the cases of adding 30 ppm, 100 ppm, 300 ppm and 500 ppm of petroleum they were subject to growth acceleration after 120 minutes, but the degree of growth acceleration increased with the increase of the amount added.

(3) Strains of the 6th generation operating on the (S-W) culture medium which were weakened were not subject to growth acceleration in case of the amount of petroleum added being 10 ppm. When the amount added was 30 ppm, 100 ppm, 300 ppm or 500 ppm, they were subjected to growth acceleration for the first time after 180 minutes.

(4) Strains of the 8th generation operating on the (S-W) culture medium were not subject to growth acceleration in case of adding 10 ppm or 30 ppm of petroleum, they were subject to slight growth acceleration after 180 minutes in the case of adding 100 ppm, 300 ppm or 500 ppm of petroleum.

(5) Strains of the 10th generation operating on the (S-W) culture medium were subject to growth acceleration only in the case when the amount of petroleum added was 300 ppm; growth acceleration slightly appeared after 180 minutes.

(6) Strains of the 12th generation operating on the (S-W) culture medium were not subjected to growth acceleration in any case; a slight tendency of growth restraint was observed in case of adding 500 ppm petroleum.

(7) Strains of the 14th–18th generation showed resuls similar to the strains of the 12th generation, i.e., they were not subject to growth acceleration in any case. Strains of the 13th and 14th generations were subject to growth restraint in case of adding 500 ppm of crude petroleum and those of the 15th, 16th, 17th and 18th generations were subject to growth restraint in case of adding 300 ppm and 500 ppm petroleum.

Further, the growth acceleration of the bacteria of this invention is clarified by calculation of number of strains in the following Table 2, but the case of strains of the 1st generation is described in detail in this specification.

TABLE 2

| 1st generation Amount added | Elapsed time after addition of crude petroleum (minutes) | | | | | |
|---|---|---|---|---|---|---|
| | 0 | 20 | 40 | 60 | 90 | 120 |
| Comparative sample | $1 \times 10^7$ | | $1.5 \times 10^7$ | $1.8 \times 10^7$ | $2.2 \times 10^7$ | $3.4 \times 10^7$ | $5 \times 10^7$ |
| 10 ppm | $1 \times 10^7$ | | $1.5 \times 10^7$ | $1.8 \times 10^7$ | $2.4 \times 10^7$ | $3.8 \times 10^7$ | $5.6 \times 10^7$ |
| 30 ppm | $1 \times 10^7$ | | $1.5 \times 10^7$ | $1.8 \times 10^7$ | $2.5 \times 10^7$ | $4 \times 10^7$ | $6 \times 10^7$ |
| 100 ppm | $1 \times 10^7$ | | $1.5 \times 10^7$ | $1.8 \times 10^7$ | $2.6 \times 10^7$ | $4.2 \times 10^7$ | $6.2 \times 10^7$ |
| 300 ppm | $1 \times 10^7$ | | $1.5 \times 10^7$ | $1.8 \times 10^7$ | $2.6 \times 10^7$ | $4.2 \times 10^7$ | $6.2 \times 10^7$ |
| 500 ppm | $1 \times 10^7$ | | $1.5 \times 10^7$ | $1.8 \times 10^7$ | $2.6 \times 10^7$ | $4.2 \times 10^7$ | $6.2 \times 10^7$ |

As can be understood from Table 2, the same results as those (Tables 1-1 to 1-6) obtained by measurement by means of a nephelometer were obtained, namely, growth acceleration was observed 120 minutes from the addition of the crude petroleum. After 24 minutes, it was 12% higher in the case of adding 10 ppm, 20% higher in the case of adding 30 ppm and 25% higher in the case of adding 100 ppm, 300 ppm or 500 ppm, as compared to the Comparative example.

(b) Bacteria acclimated by 30 ppm of crude petroleum

The same procedure as in the case of the 500 ppm acclimation bacteria was carried out but the amounts of crude petroleum added in the logarithmic phase were 10 ppm, 30 ppm, 100 ppm and 300 ppm. The results are shown in Table 3.

TABLE 3

| Amount added | Elapsed time after addition of crude petroleum (minutes) | | | | | | | |
|---|---|---|---|---|---|---|---|---|
| | 0 | 20 | 40 | 60 | 90 | 120 | 180 | 240 |
| 1st generation | | | | | | | | |
| Comparative sample | 50 | 51 | 52 | 53 | 55 | 57 | 60 | 65 |
| 10 ppm | 50 | 51 | 52 | 53 | 55.5 | 58.5 | 61.5 | 67 |
| 30 ppm | 50 | 51 | 52 | 53 | 55.5 | 58.5 | 62 | 68 |
| 100 ppm | 50 | 51 | 52 | 53 | 55.5 | 58.5 | 62 | 68 |
| 300 ppm | 50 | 51 | 52 | 53.5 | 55.5 | 58.5 | 62 | 68 |
| 4th generation | | | | | | | | |
| Comparative sample | 50 | 51 | 52 | 53.5 | 56 | 58.5 | 62 | 67 |
| 10 ppm | 50 | 51 | 52 | 53.5 | 56 | 59 | 63 | 68 |
| 30 ppm | 50 | 51 | 52 | 53.5 | 56 | 59 | 63 | 68 |
| 100 ppm | 50 | 51 | 52 | 53.5 | 56 | 59 | 63 | 68 |
| 300 ppm | 50 | 51 | 52 | 53.5 | 56 | 59 | 63 | 68 |
| 6th generation | | | | | | | | |
| Comparative sample | 50 | 51 | 52 | 53.5 | 56 | 58.5 | 62 | 67 |
| 10 ppm | 50 | 51 | 52 | 53.5 | 56 | 58.5 | 62.5 | 67.5 |
| 30 ppm | 50 | 51 | 52 | 53.5 | 56 | 58.5 | 63 | 68 |
| 100 ppm | 50 | 51 | 52 | 53.5 | 56 | 58.5 | 63 | 68 |
| 300 ppm | 50 | 51 | 52 | 53.5 | 56 | 58.5 | 62 | 67 |
| 8th generation | | | | | | | | |

TABLE 3-continued

| Amount added | Elapsed time after addition of crude petroleum (minutes) | | | | | | | |
|---|---|---|---|---|---|---|---|---|
| | 0 | 20 | 40 | 60 | 90 | 120 | 180 | 240 |
| Comparative sample | 50 | 51 | 52 | 53.5 | 56 | 58.5 | 62 | 67 |
| 10 ppm | 50 | 51 | 52 | 53.5 | 56 | 58.5 | 63 | 68 |
| 30 ppm | 50 | 51 | 52 | 53.5 | 56 | 58.5 | 63 | 68 |
| 100 ppm | 50 | 51 | 52 | 53.5 | 56 | 58.5 | 63 | 68 |
| 300 ppm | 50 | 51 | 52 | 53.5 | 56 | 58.5 | 62 | 67 |
| 10th generation | | | | | | | | |
| Comparative sample | 50 | 51 | 52 | 53.5 | 56 | 58.5 | 62 | 67 |
| 10 ppm | 50 | 51 | 52 | 53.5 | 56 | 58.5 | 62 | 67 |
| 30 ppm | 50 | 51 | 52 | 53.5 | 56 | 58.5 | 62 | 67 |
| 100 ppm | 50 | 51 | 52 | 53.5 | 56 | 58.5 | 62.5 | 67 |
| 300 ppm | 50 | 51 | 52 | 53.5 | 56 | 58.5 | 62 | 67 |
| 12th generation | | | | | | | | |
| Comparative sample | 50 | 51 | 52 | 53.5 | 56 | 58.5 | 62 | 67 |
| 10 ppm | 50 | 51 | 52 | 53.5 | 56 | 58.5 | 62 | 67 |
| 30 ppm | 50 | 51 | 52 | 53.5 | 56 | 58.5 | 62 | 67 |
| 100 ppm | 50 | 51 | 52 | 53.5 | 56 | 58.5 | 62 | 67 |
| 300 ppm | 50 | 51 | 52 | 53.5 | 56 | 57.5 | 60.5 | 65 |

As will be obvious from Table 3, the degree of growth acceleration was similar to the case of the 500 ppm acclimation strain, even though the amount of crude petroleum was small.

When strains of the 14th–18th generations were used, they were not subject to growth acceleration; likewise in the case of the strain of the 12th generation, and multiplication was restrained by the addition of 300 ppm as compared with the comparative sample.

The (S-W) culture medium was used in the above described procedures. However, in the case of using a more eutrophic culture medium comprising peptone or a meat extract, the results obtained were not essentially different from those obtained in case of using the (S-W) culture medium, and growth acceleration was observed after 120 minutes from the addition of the oil.

Further, concerning the death of the bacteria having a high degree of growth acceleration of the present invention, the 500 ppm and 30 ppm acclimation bacteria died after 3 days when they were introduced into the brine or fresh water. The effect was noted that the life span of the bacteria gradually extended with lowering degrees of growth acceleration.

(2) Change of emulsification capability depending on the operating generation in the (S-W) culture medium (a) Using bacteria acctimated by 500 ppm of crude petroleum (culture medium: brine+crude petroleum 500 ppm)

TABLE 4

| Operating generation | Degree of emulsification | | | | | | | |
|---|---|---|---|---|---|---|---|---|
| | 12 | 24 | 48 | 72 | 96 | 120 | 168 | 240 hrs. |
| 1 | + | ++ | +++ | ++ | +⊥ | + | ⊥ | — |

TABLE 4-continued

| Operating generation | Degree of emulsification | | | | | | | |
|---|---|---|---|---|---|---|---|---|
| | 12 | 24 | 48 | 72 | 96 | 120 | 168 | 240 hrs. |
| 4 | ⊥ | +⊥ | ++ | ++ | +⊥ | + | ⊥ | ⊥ |
| 6 | − | + | +⊥ | ++ | ++ | +⊥ | + | ⊥ |
| 8 | − | ⊥ | + | +⊥ | +⊥ | +⊥ | + | ⊥ |
| 10 | − | − | + | +⊥ | +⊥ | +⊥ | + | + |
| 12 | − | − | + | +⊥ | +⊥ | +⊥ | + | + |
| 14 | − | − | −∼⊥ | ⊥ | ⊥ | ⊥ | ⊥ | ⊥ |
| 16 | − | − | − | − | − | − | − | − |
| 18 | − | − | − | − | − | − | − | − |

+++: Extraordinary superior growth
++: Very good growth
+⊥: Good growth
+: Normal growth
⊥: Poor growth
−: No growth As will be obvious from above Table 4, the emulsification ability of the bacteria gradually deteriorates with increasing number of generations. In addition, the bacteria is of the wide range from the case that generation of the emulsification phenomena is shown in the early stage to the case that it is shown in a delayed stage. Further, and more importantly, it was found that even the bacteria of the 12th-14th generation (which were not subject to growth acceleration by addition of crude petroleum) slightly cause emulsification after 48 hours from inoculation of the bacteria. This fact is an important key for solving the relation between the growth acceleration and the emulsification.

(b) Using bacteria acclimated by 30 ppm of crude petroleum (culture medium: brine+crude petroleum 30 ppm)

TABLE 5

| Operating generation | Degree of emulsification | | | | | | | |
|---|---|---|---|---|---|---|---|---|
| | 12 | 24 | 48 | 72 | 96 | 120 | 168 | 240 hrs |
| 1 | + | ++ | +++ | ++ | + | ⊥ | − | − |
| 4 | ⊥ | +⊥ | ++ | ++ | + | ⊥ | ⊥ | − |
| 6 | − | + | + | +⊥ | +⊥ | + | ⊥ | ⊥ |
| 8 | − | ⊥ | + | ++ | +⊥ | + | ⊥ | ⊥ |
| 10 | − | − | + | ++ | ++ | +⊥ | + | ⊥ |
| 12 | − | − | ⊥ | + | + | + | + | + |
| 14 | − | − | −∼⊥ | ⊥ | ⊥ | ⊥ | ⊥ | − |
| 16 | − | − | − | − | − | − | − | − |
| 18 | − | − | − | − | − | − | − | − |

As will be obvious from Table 5, results similar to those in the case of using 500 ppm of acclimation bacteria are obtained. It will be understood that emulsification is caused by the addition of the crude petroleum even if the bacteria are not subject to growth stimulation.

(3) Degree of crude petroleum removability depending on operating generation in (S-W) culture medium
(a) Using bacteria acclimated by 500 ppm of crude petroleum (culture medium: brine+crude petroleum 500 ppm)

TABLE 6

| Operating generation | Crude petroleum residual amount (ppm) | | | | | |
|---|---|---|---|---|---|---|
| | 24 | 48 | 72 | 96 | 120 | 168 hrs |
| 1 | 280 | 60 | 5 | 2 | 1 | 1 |
| 4 | 330 | 90 | 25 | 10 | 25 | 2 |
| 6 | 360 | 180 | 80 | 30 | 7 | 5 |
| 8 | 370 | 280 | 130 | 70 | 30 | 25 |
| 10 | 400 | 320 | 200 | 100 | 60 | 50 |
| 12 | 450 | 370 | 300 | 250 | 220 | 200 |
| 14 | 470 | 400 | 350 | 300 | 270 | 250 |
| 16 | 480 | 440 | 420 | 380 | 350 | 330 |
| 18 | 500 | 500 | 500 | 500 | 500 | 500 |

As will be obvious from Table 6, when 500 ppm of crude petroleum are added, the residual amount of crude petroleum after 168 hours is only 1 ppm (1/500 of the original value) in the case of the strain of the 1st generation, only 2 ppm (1/250 of the original volume) in case of the strain of the 4th generation, 5 ppm (1/100 of the original value) in case of the strain of the 6th generation, 25 ppm (1/50 of the original value) in the case of the strain of the 8th generation, and 50 ppm (1/10 of the original value) in the strain of the 10th generation (which shows the minimum growth acceleration). Though the removal ratio gradually deteriorates, the petroleum residual amount decreases by one order, compared with the original amount.

In destination, in the case of the strain of the 125h generation—which does not show growth acceleration any longer—the removal ability rapidly deteriorated and was only 1/2.5 the original value. Thus, the bacteria cannot be used as a petroleum removing agent.

In the case of the strain of the 14th generation, 250 ppm remained (½ of the original volume). In the case of the strain of the 16th generation—which lost its emulsifying ability—the removal ratio deteriorated and 300 ppm remained (⅔ of the original value). In the case of the strain of the 18th generation, the strain did not grow in the culture medium (brine+crude petroleum 500 ppm) and the petroleum removal ratio was 0.

Further, when the cultivation was continued for 240 hours, the petroleum residual amount became less than 2 ppm in the case of even the strain of the 6th generation which showed a slight growth acceleration, and, on the other hand, the petroleum residual amount was about 198 ppm in the case of strains which were no longer show growth acceleration and have only emulsifying ability, for example, the strain of the 12th generation. This means that growth acceleration bacteria according to the present invention show a remarkably excellent petroleum removal ability as compared with bacteria which show only emulsifying ability, i.e., it can be understood that the growth acceleration bacteria according to the present invention show remarkably good results in hydrocarbon consumption as compared with mere emulsification bacteria and that they are further different from conventional assimilation bacteria.

(b) Using bacteria acclimated by 30 ppm of crude petroleum (culture medium: brine+crude petroleum 30 ppm)

TABLE 7

| Operating generation | Crude petroleum residual amount (ppm) | | | | | |
|---|---|---|---|---|---|---|
| | 24 | 48 | 72 | 96 | 120 | 168 hrs |
| 1 | 5 | 1 | 0.5 | 0.4 | 0.4 | 0.4 |
| 4 | 10 | 3 | 2 | 1 | 0.5 | 0.5 |
| 6 | 15 | 7 | 3 | 2 | 1 | 1 |
| 8 | 18 | 10 | 6 | 4 | 2 | 1.5 |
| 10 | 22 | 15 | 10 | 6 | 4 | 2 |
| 12 | 25 | 20 | 17 | 14 | 12 | 10 |
| 14 | 27 | 22 | 18 | 16 | 15 | 15 |
| 16 | 28 | 24 | 22 | 20 | 18 | 18 |
| 18 | 30 | 30 | 30 | 30 | 30 | 30 |

As will be obvious from Table 7, removal of crude petroleum gradually deteriorates with an increase in the number the generation involved in the case of adding 30 ppm of crude petroleum similar to the case of adding 500 ppm of crude petroleum. Further the degree of consumption remarkably deteriorates in the case of using strains which were not subject growth acceleration by the addition of the crude petroleum. Namely, when cultivation is continued for 240 hours, the crude petroleum residual amount becomes lower than 0.8 ppm even in the case of the strain of the 6th generation which shows the lowest degree of growth acceleration, and in the case of the strains which were no longer subject to growth acceleration, the crude petroleum residual amount is still 10 ppm in the case of the strain of the 12th generation. Thus, growth acceleration bacteria and emulsification bacteria which do not show growth acceleration are very different each other from the viewpoint of petroleum consumption, and the growth acceleration bacteria of the present invention are further different from mere assimilation bacteria.

(4) Interrelationship between growth acceleration, emulsification and crude petroleum consumption.

The results of the above procedures (1)–(3) are summarized below.

(a) Case of 500 ppm acclimation bacteria (culture medium: brine+crude petroleum 500 ppm)

TABLE 8

| Operating generation in (S-W) | Growth acceleration by addition of crude petroleum | Emulsification | Assimilation ability | Residual amount of crude petroleum (after 7 days) |
|---|---|---|---|---|
| 1 | o | o | o | (1 ppm) |
| 2 | o | o | o | |
| 3 | o | o | o | |
| 4 | o | o | o | (2 ppm) |
| 5 | o | o | o | |
| 6 | o | o | o | (5 ppm) |
| 7 | o | o | o | |
| 8 | o | o | o | (25 ppm) |
| 9 | o | o | o | |
| 10 | o | o | o | (50 ppm) |
| 11 | x | o | o | |
| 12 | x | o | o | (200 ppm) |
| 13 | x | o | o | |
| 14 | x | o | o | (250 ppm) |
| 15 | x | x | o | |
| 16 | x | x | o | (330 ppm) |
| 17 | x | x | o | |
| 18 | x | x | x | (500 ppm) | o: observed
x: not observed (b) Case of 30 ppm acclimation bacteria (culture medium: brine+crude petroleum 30 ppm)

TABLE 9

| Operating generation in (S-W) | Growth acceleration by addition of crude petroleum | Emulsification | Assimilation ability | Residual amount of crude petroleum (after 7 days) |
|---|---|---|---|---|
| 1 | o | o | o | (0.4 ppm) |
| 2 | o | o | o | |
| 3 | o | o | o | |
| 4 | o | o | o | (0.5 ppm) |
| 5 | o | o | o | |
| 6 | o | o | o | (1 ppm) |
| 7 | o | o | o | |
| 8 | o | o | o | (1.5 ppm) |
| 9 | o | o | o | |
| 10 | o | o | o | (2 ppm) |
| 11 | x | o | o | |
| 12 | x | o | o | (10 ppm) |
| 13 | x | o | o | |
| 14 | x | o | o | (15 ppm) |
| 15 | x | o | o | |
| 16 | x | x | o | (18 ppm) |
| 17 | x | x | o | |
| 18 | x | x | x | (30 ppm) |

Figure 2:
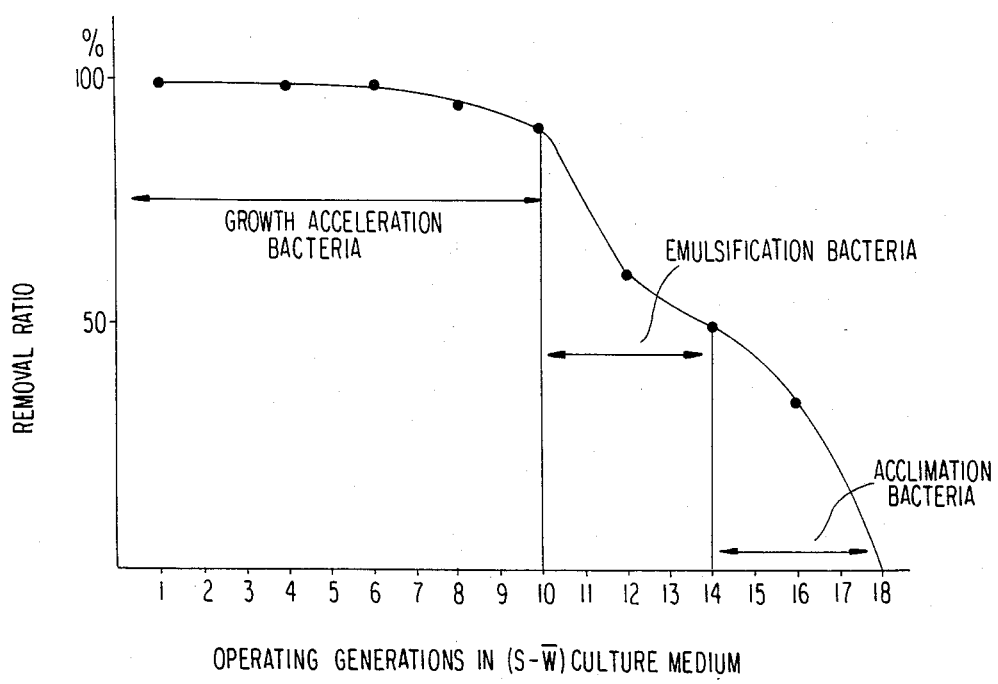
FIGS. 2 and 3 are graphs which illustrate the properties of the strain according to this invention concerning growth acceleration, emulsification and assimilation.
Figure 3:
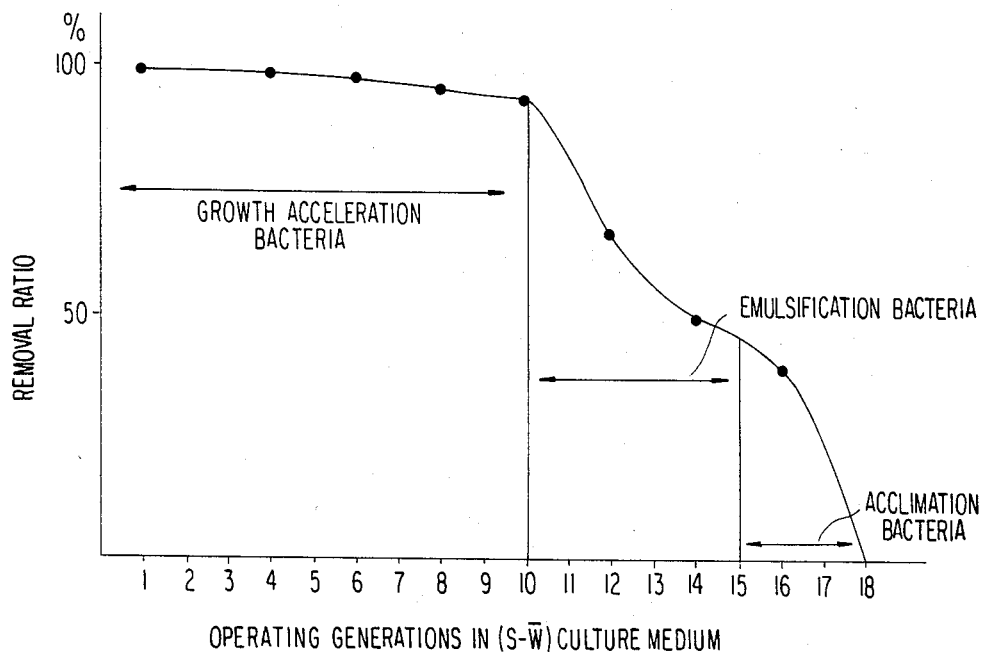

The results of Tables 8 and 9 are presented in FIGS. 2 and 3 as graphs.

The above described results were obtained using FERM BP-63, but the interrelation ship between growth acceleration by crude petroleum, emulsification and assimilation are essentially similar in the case of using FERM BP-64 and other bacteria. This fact was confirmed not only by testing of deterioration in the ability of high-powered growth acceleration bacteria but also that of increase in the ability of bacteria produced by induction.

The results shown in these Tables and in the drawings relates various characteristics required for purification of petroleum pollution by microbes Growth Stimulation Angle In order to determine the angle $\theta$, it is first necessary to obtain a $\mu$ value. The specific growth speed $\mu$ is expressed by the following formula.

$$\frac{2.303(\log n_2 - \log n_1)}{t_2 - t_1}$$

where $t_1$ and $t_2$ are time; and $n_1$ and $n_2$ are the number of bacterial cells at the time of $t_1$ and $t_2$, respectively. Larger $\mu$ values show higher growth rates, and lower $\mu$ values show slower growth rates.

The growth angle can be calculated on the basis of the following.

The strains used in this invention are selected on the basis of the angle (growth angle) formed between the growth curve of a strain which is cultured on the Stephanson Wetham medium and the growth curve of the strain which is cultured on the Stephanson Wetham medium added a petroleum hydrocarbon. The procedure of calculation is described below with reference to FIG. 4.

Figure 4:
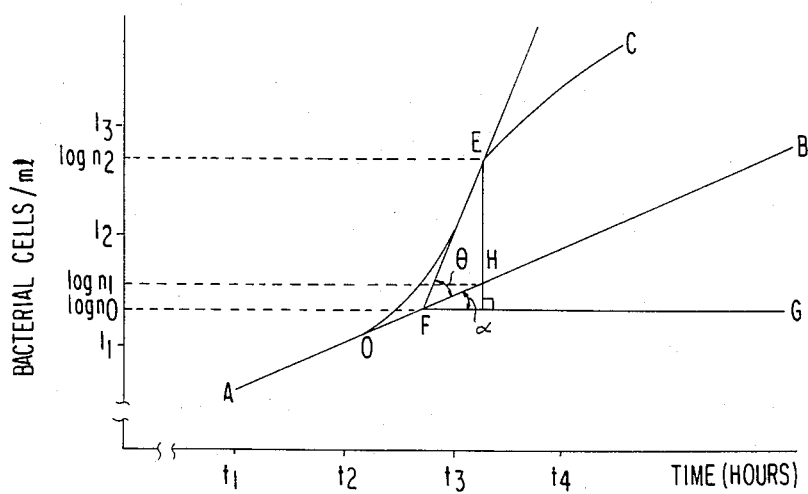
FIG. 4 is a graph schematically illustrating growth stimulation angle ($\theta$).

In FIG. 4, AB represents the growth line of a bacterial strain in its logarithmic growth period in a Stephanson Wetham culture medium not containing petroleum hydrocarbon. After the addition of the petroleum hydrocarbon, stimulation of growth begins to appear at point 0, and a line OC is drawn. The point formed by the intersection of a tangential line EF having the highest gradient (the line showing the maximum $\mu$ value, i.e., the specific growth speed) with a line OB is supposed to be a point F, and the line extending from the point F and being parallel to the axis of abscissas is supposed to be a line FG. Further, a perpendicular line is drawn from the point E to a line FG, and a point at which the perpendicular line intersects with a line AB is supposed to be a point H. The number of strains/cc at point E is log $n_2$; the number of strains at H is log n, and the number of strains in point F is log $n_o$. Furthermore, $\angle BFG = \alpha$ $\angle BFE = \theta$ If the interval between $l_1$, $l_2$ of the logarithmic values (1, 2, 3, 4 ... 8, 9, 10) of the number of strains is made equal to the interval between $t_1$, $t_2$ of the time (hours), $\alpha$ and $\beta$ can be calculated using the following equations.

$$\tan \alpha = \frac{d \log (n_1 - n_0)}{dt} = \frac{\mu'}{2.303} \quad (1)$$

$\mu'$ ... $\mu$ value of OB $$\tan (\alpha + \theta) = \frac{d \log (n_2 - n_0)}{dt} = \frac{\mu''}{2.303} \quad (2)$$

$\mu''$ ... maximum $\mu$ value of EF $$(\alpha + \theta) - \alpha = \theta \quad (3)$$

If the maximum $\mu$ value is substituted in the above equation, the angle formed by the intersection of the growth curve in a basic medium [S-W] with the growth curve which results from the addition of the petroleum hydrocarbon can be calculated in regard to strains of the same species which differ from each other in purifying power.

EP value

As a result of investigation for $\theta$ and $\mu$ value, the inventor has found an index to know an ability to remove hydrocarbons EP-value in relation to $\theta$ and $\mu$ value.

EP-value represents a hydrocarbon purifying ability and is obtained by the following formula.

$$\mu \times \sqrt{\theta} = EP(\theta = 0)$$

wherein $\theta$ represents a growth stimulation angle and $\mu$ represents a specific growth speed.

In the following Table, a relation between EP-value and an amount of remaining crude oil is shown using various bacteria in the case of purification of 500 ppm crude oil in brine.

TABLE 12

| $\mu$ | $\theta°$ | EP-value | \multicolumn{6}{c}{Amount of Remaining Crude Oil ppm} |
|---|---|---|---|---|---|---|---|---|
| | | | 24 | 48 | 72 | 96 | 120 | 168 hrs. |
| 0.4 | 0.05 | 0.09 | 450 | 360 | 290 | 240 | 200 | 180 |
| 0.4 | 0.07 | 0.106 | 400 | 330 | 210 | 120 | 90 | 65 |
| 0.4 | 0.1 | 0.13 | 400 | 320 | 250 | 110 | 85 | 60 |
| 0.4 | 0.4 | 0.25 | 380 | 300 | 150 | 85 | 50 | 40 |
| 0.4 | 0.5 | 0.28 | 380 | 300 | 140 | 80 | 40 | 35 |
| 0.4 | 1.0 | 0.40 | 370 | 200 | 100 | 50 | 20 | 10 |
| 0.4 | 1.6 | 0.50 | 330 | 90 | 25 | 10 | 5 | 2 |
| 0.4 | 2.3 | 0.60 | 280 | 60 | 8 | 3 | 1.5 | 1 |
| 0.4 | 3.0 | 0.70 | 250 | 50 | 5 | 2 | 1.0 | 0.7 |
| 0.6 | 0.02 | 0.085 | 450 | 380 | 310 | 250 | 210 | 190 |
| 0.6 | 0.03 | 0.104 | 400 | 330 | 210 | 120 | 90 | 65 |
| 0.6 | 0.5 | 0.42 | 360 | 180 | 90 | 45 | 15 | 8 |
| 0.6 | 1.4 | 0.7 | 250 | 50 | 5 | 2 | 1 | 0.7 |

The Table 12 shows that, for example, an amount of crude oil reduced to 0.7 ppm after 7 days (168 hours) using bacteria having 0.7 of EP-value ($\theta = 3°$, $\mu = 0.4$).

As is shown in the following Table 13 to 16, it becomes apparent that bacteria having the same EP value values show the same amount of remaining crude oil, even if the bacteria have different $\theta$ and $\mu$ value each other. The used polluted brine contains 500 ppm of crude oil.

TABLE 13

| $\mu$ | $\theta°$ | EP-value | Amount of Remaining Crude Oil after 168 hrs. (ppm) |
|---|---|---|---|
| 0.3 | 0.2 | 0.13 | 60 |
| 0.4 | 0.1 | 0.13 | 60 |
| 0.5 | 0.07 | 0.13 | 60 |
| 0.6 | 0.05 | 0.13 | 60 |
| 0.7 | 0.035 | 0.13 | 60 |

TABLE 14

| $\mu$ | $\theta°$ | EP-value | Amount of Remaining Crude Oil after 168 hrs. |
|---|---|---|---|
| 0.3 | 0.9 | 0.28 | 35 |
| 0.4 | 0.5 | 0.28 | 35 |
| 0.5 | 0.33 | 0.28 | 35 |
| 0.6 | 0.22 | 0.28 | 35 |
| 0.7 | 0.16 | 0.28 | 35 |

TABLE 15

| $\mu$ | $\theta°$ | EP-value | Amount of Residual Crude Oil after 168 hrs. (ppm) |
|---|---|---|---|
| 0.3 | 1.8 | 0.4 | 10 |
| 0.4 | 1 | 0.4 | 10 |
| 0.5 | 0.65 | 0.4 | 10 |
| 0.6 | 0.45 | 0.4 | 10 |
| 0.7 | 0.35 | 0.4 | 10 |

TABLE 16

| $\mu$ | $\theta°$ | EP-value | Amount of Residual Crude Oil after 168 hrs. (ppm) |
|---|---|---|---|
| 0.3 | 5.5 | 0.7 | 0.7 |
| 0.4 | 3 | 0.7 | 0.7 |
| 0.5 | 2 | 0.7 | 0.7 |
| 0.6 | 1.4 | 0.7 | 0.7 |
| 0.7 | 1 | 0.7 | 0.7 |

In the present invention, bacteria having 0.1 or more, preferably 0.3 or more of EP-value are used to remove hydrocarbons.

Microscopic observation and morphological characteristics of the present bacteria FERM BP-63 and 64 are shown in the following Tables 15 to 17.

TABLE 17

| | FERM BP-63 | FERM BP-64 |
|---|---|---|
| Gram | — | — |
| Shape | middle rod | middle rod |
| Spore | — | — |
| Capsule | — | — |
| Motility | + | + |
| Culturing Condition | faculative anaerobe | faculative anaerobe |
| Colony | large round moistend colonies | large round moistend colonies |
| Projection | normal | normal |
| Surface | smooth | smooth |
| Color | grayish white to semitransparent mucous | milky white to semitransparent mucous |
| Circumference | circle | circle |

TABLE 18

| (General Properties) | | |
|---|---|---|
| | FERM BP-68 | FERM BP-64 |
| Ammonia-production | — | — |
| H$_2$S-production | — | — |
| Indole-production | — | — |
| Catalase-production | + | + |
| Pigment-production | — | — |

TABLE 18-continued

| (General Properties) | | |
|---|---|---|
| | FERM BP-68 | FERM BP-64 |
| Decomposition of urea | − | − |
| Utilization of citric acid | − | − |
| Gelatin liquefaction | − | − |
| V.P. reaction | − | − |
| Nitration of nitrates | − | − |

TABLE 19

| (Ability to decompose sugars) | | |
|---|---|---|
| | FERM BP-63 | FERM BP-64 |
| Glucose | + | + |
| Starch | + | + |
| Melezitose | − | − |
| Maltose | − | − |
| Raffinose | − | − |
| Fractose | + | + |
| Melobiose | − | − |
| Xylose | − | − |
| Solbitol | − | − |
| Mannitol | − | − |
| Inositol | − | − |
| Arabinose | − | − |
| Lactose | − | − |
| Mannose | + | + |
| Sucrose | − | + |
| Salicine | − | + |

As the results of the experiments about prior art microbes assimilation of petroleum is known, but studies concerning emulsification have been barely carried out. Accordingly, the existence and phenomena of growth acceleration bacteria are unexpected from prior art knowledge.

EXAMPLE 1

50 liters of a culture medium comprising 0.5 g of crude petroleum comprising Khafuji crude petroleum and 1000 ml of brine collected from brine near Akashi City were poured into a water tank (90 cm × 50 cm × 40 cm). 20 ml of a bacteria solution acclimated by 500 ppm of crude petroleum obtained according to the present invention was inoculated on the above described culture medium and incubated at 18° C. for 42 hours. the resultant cultured solution was cooled to about 10° C. and subjected to centrifugal separation (10,000×g) to obtain 60 g of a mixture of bacteria and a crude petroleum emulsion used to form Preparations (A)–(D) below. (Preparation B) 0.44 g of starch (potato), 0.001 g of crude petroleum were added to 10 g of the above described mixture and well mixed. The resultant mixture was dried in vacuum (−750∼ −760 mmHg) to an 8 wt% water contact. 2.9 g of the resultant dry material was put in a glass bottle and the bottle was filled with an inert gas such as $CO_2$ or $N_2$. The effective preservation period of the resultant agent was more than 20 days at room temperature and more than 3 months in a refrigerator at 5°–8° C.

(Preparation B)

0.44 g of starch, 0.001 g of crude petroleum and 0.11 g of cystine were added to 10 g of the above described mixture and well mixed. 3.01 g of the agent having an 8 wt% water content was produced in the same manner as for Agent A and enclosed in a glass bottle with $N_2$ gas. The effective preservation period of the resultant agent was more than 20 days at a room temperature and more than 3 months at 5°–8° C.

(Agent C)

0.4 g of starch of potato was added to 10 g of the above described mixture and well mixed. The resultant mixture was dried in a vacuum (−750 to −760 mmHg) to obtain 2.5 g of agent. The resultant agent was effective for long periods of time when stored at room temperature.

(Agent D)

0.1 g of cystine and 0.001 g of crude petroleum were added to 10 g of the above described mixture and well mixed. The resultant mixture was dried in a vacuum to obtain 2.1 g of agent. The resultant agent was effective for long periods of time when storage at room temperature.

EXAMPLE 2

12.5 ml of crude petroleum was added dropwise to an acrylic resin tank having a volume of about 33 liters (length 26 cm; width 45 cm; depth 30 cm). After the crude petroleum was sufficiently applied to the bottom and the sides of the tank, 27 liters of brine were charged thereto. The amount of crude petroleum in the brine in this case was 500 ppm. The temperature of the brine was controlled at 180° C. and the system was aerated using an appropriate apparatus provided on the tank as later described. A cultivating solution of the crude petroleum assimilation bacteria (FERM BP-63) according to the present invention (incubated on a culture medium comprising brine and crude petroleum for 48 hours at 18° C.) was added in an amount of 9 mg (1/3000 the volume of the brine). 9 mg of the cultivating solution consisted of 3 mg of 500 ppm acclimation bacteria, 3 mg of 100 ppm acclimation bacteria and 3 mg of 30 ppm acclimation bacteria. 24 hours after the beginning of the run, aeration was carried out at a rate of 2 liters/minute.

From the beginning of the run the brine was periodically examined and the emulsification state of the brine in the water tank and the state of crude petroleum adhesion on the surface of the walls of the tank were observed with the naked eye. The crude petroleum content (measured by UV) and cell counts per 1 cc were also measured. The results are shown in Table 10.

TABLE 10

| Time | Emulsification state | Crude petroleum adhesion state on sides of tank | Crude petroleum content (ppm) | Cell count/cc |
|---|---|---|---|---|
| At addition | None | Thick adhesion on the whole side | | 1 × 10$^8$ |
| 4 hrs. | Emulsification begins very slightly | Thick adhesion on the whole side | | |
| 7 hrs. | Slight emulsification | Thick adhesion on the whole side | | |
| 8 hrs. | Emulsification proceeds | Thick adhesion on the whole side | | |
| 12 hrs. | Brine becomes completely cloudy | Thick adhesion on the whole side | 300 ppm | |
| 24 hrs | Emulsification proceeds and there is no trans- | Slight adhesion. Amount of crude petroleum be- | 180 ppm | 8 × 10$^8$ |

TABLE 10-continued

| Time | Emulsification state | Crude petroleum adhesion state on sides of tank | Crude petroleum content (ppm) | Cell count/cc |
|---|---|---|---|---|
| | parency | comes slightly lowered (about 80% of original state) | | |
| 48 hrs. | Emulsification becomes remarkable | Adhesion of about 50% of original | 30 ppm | $3.5 \times 10^9$ |
| 72 hrs. | Emulsification is remarkable | Adhesion of about 20% of original | 0.5 ppm | $2.5 \times 10^9$ |
| 96 hrs. | Cloudiness somewhat reduced | Adhesion is hardly observed | 0.3 ppm | $3 \times 10^8$ |
| 120 hrs. | Cloudiness reduced and transparency increased | Traces not observed | 0.2 ppm | $6 \times 10^7$ |
| 144 hrs | Transparency somewhat increased (some cloudiness) | Traces not observed | 0.2 ppm | $1 \times 10^7$ |
| 168 hrs. | Transparency remarkably increased (slight cloudiness) | Traces not observed | 0.2 ppm | $2 \times 10^5$ |
| 192 hrs | Nearly transparent (very slight cloudiness) | Traces not observed | 0.2 ppm | 0/cc extinction |

As is obvious from Table 10, emulsification began 4 hours after the addition of the bacteria and rapidly increased by 7 hours, becoming remakably high after 48–72 hours and gradually deteriorating thereafter while transparency rapidly increased after 144 hours and the system became nearly transparent after 192 hours.

On the other hand, crude petroleum thickly adhered to the walls gradually decreased after about 24 hours and the adhered crude petroleum was hardly observed after 96 hours. Further, the crude petroleum content in the brine rapidly decreased to 180 ppm after 24 hours, 30 ppm after 48 hours and 0.5 ppm after 72 hours, and gradually decreased to 0.3 ppm after 96 hours and 0.2 ppm after 120 hours. After 120 hours, the same results were shown (removal ratio: 99.96%).

The crude petroleum assimilation bacteria in the brine had an initial cell count of $1 \times 10^6$/cc, which increased to $5 \times 10^8$ after 24 hours and $3.5 \times 10^9$ after 48 hours. The cell counts gradually decreased thereafter to become $2.5 \times 10^9$ after 72 hours, $3 \times 10^8$ after 96 hours, $6 \times 10^7$ after 120 hours and $1 \times 10^7$ after 144 hours. The bacteria then showed a tendency to die and the cell count became $2 \times 15^5$ after 168 hours. After 192 hours, living cells were not observed.

At elapsed time of 192 hours (8 days) from the beginning of the run, the tank had a good appearance, i.e., the same as before pollution. Further, the brine was clean and did not differ from common brine, except it was very slightly cloudy.

EXAMPLE 3

The same procedure was carried out except that the crude petroleum content was 30 ppm and crude petroleum 30 ppm acclimation bacteria were used. Results of are shown in Table 11.

TABLE 11

| | State of emulsification | Crude petroleum content | Cell counts/cc |
|---|---|---|---|
| At addition | None | 30 ppm | $3 \times 10^5$ |
| 4 hrs. | Emulsification begins very slightly | 30 ppm | |
| 7 hrs. | Slight emulsification | 29 ppm | |
| 8 hrs. | Emulsification somewhat proceeds | 27 ppm | |

TABLE 11-continued

| | State of emulsification | Crude petroleum content | Cell counts/cc |
|---|---|---|---|
| 12 hrs. | Whole of the brine is cloudy | 23 ppm | |
| 24 hrs. | Emulsification proceeds no sense of transparency | 3 ppm | $4 \times 10^8$ |
| 48 hrs. | Emulsification is remarkable | 0.3 ppm | $1.2 \times 10^9$ |
| 72 hrs. | Cloudiness reduced sense of transparency appears | 0.2 ppm | $5 \times 10^8$ |
| 96 hrs. | Transparency increased | 0.15 ppm | $2 \times 10^7$ |
| 120 hrs. | Transparency remarkably increased | 0.15 ppm | $3 \times 10^5$ |
| 144 hrs. | Nearly transparent | 0.15 ppm | 0 |

As will be obvious from Table 11, emulsification began after 4 hours of the run and gradually increased with the passage of time. It became remarkable after 36–48 hours, whereafter it deteriorated and the sense of transparency rapidly appeared after about 96 hours. After 144 hours, the system became nearly transparent.

On the other hand, the crude petroleum content of the brine rapidly decreased to become 3 ppm—1/10 of the original value—after 24 hours and 0.3 ppm—1/100 of the original value—after 48 hours. It gradually decreased to become 0.2 ppm after 72 hours and 0.15 ppm after 96 hours. After 96 hours, the same results were shown (removal ratio: 99.5%).

Further, the assimilation bacteria had an initial cell count of $3 \times 10^5$, which increased to $4 \times 10^8$ after 24 hours and $1.2 \times 10^9$ after 48 hours. The cell counts decreased thereafter to $5 \times 10^8$ after 72 hours and $2 \times 10^7$ after 96 hours. Thereafter the bacteria rapidly died and the cell count became only $3 \times 10^5$ after 120 hours. After 144 hours, all bacteria were dead.

At an elapsed time of 144 hours (6 days) from the beginning of the fun, the tank had a good appearance and the brine in the tank was clean.

Further, in an examination regarding the reactivity of bacteria showed growth acceleration by crude petroleum with respect to each component in the crude petroleum, rapid growth acceleration was shown for light oil when the degree of acclimation was very small, but acclimation was difficult for B-heavy oil and more difficult for C-heavy oil. However, by continuing processing similar to the above described five steps, assimilation, emulsification and growth acceleration appeared in a manner similar to the case of using crude petroleum. When growth acceleration appeared, the acclimation for B-heavy oil and C-heavy oil was more easily carried out than in the case of crude petroleum. Further, the fact that consumption of B- and C-heavy oil was well carried out and the amount of residual components was very small meant that almost all components were taken by the bacteria. Hitherto, the term "petroleum protein" has been used by choice. In this case, bacteria which were subjected to growth acceleration by the used petroleum components have not been known. Further, the yield is of course better in case of the growth acceleration bacteria.

In addition, a process for treating oil by adding bacteria which have been subjected to growth acceleration by oil to an activated sludge, namely, by producing an enriched activated sludge, is an example of the application of bacteria according to the present invention, by which good water can be effectively discharged when tanks on the shore are cleaned. The following is an example of applying the bacteria according to the present invention to an activated sludge.

EXAMPLE 4

(1) Cultivating liquid containing bacteria of the present invention acclimated by 500 ppm, 100 ppm or 30 ppm of crude petroleum, in amount of 1:1:1, which were subject to growth acceleration by the crude petroleum, were charged into an activated sludge in an amount of 1/10 by the volume of the activated sludge used in Example 3. Petroleum containing waste liquor was flowed into the sludge and the flow rate gradually increased, an initial flowing rate being 3 cc/minute and the final flowring rate being 10 cc/minute. The enriched activated sludge had a processing capability 70 times that of activated sludge containing no bacterium. Further, it had a processing ability 15 times that of activated sludge to which known petroleum assimilation bacteria were added. The activated sludge was obtained according to the procedures described in, for example, U.K. Pat. No. 1,277,632.

(2) Since the adaptability of protozoa in the activated sludge is remarkably inferior to that of bacteria, it is sometimes preferred to initially process only with the bacteria when petroleum containing waste liquor having a large load variation is processed. Thus, growth acceleration bacteria subject to group acceleration by 500 ppm, 100 ppm or 30 ppm of crude petroleum were incubated in a tank having a volume of 30 liters to have a cell count of $10^9$/ml. To the cultivated material, crude petroleum containing waste liquor was added in an amount of 10 ml/minute. The resultant waste liquor mixture containing the bacteria was flowed into the protozoa inhabiting tank to carry out purification. The crude petroleum content detected in the processed liquid was less than 1/250 of the original volume.

EXAMPLE 5

The crude petroleum mixture comprising Khafji crude oil and Iranian heavy oil (1:1) was applied to the wall and the bottom of a drum having a volume of 50 liters. After standing for 3 days, the adhered oil was separated as much as possible using the pressure of the brine. The Iranian heavy oil has a following physical properties; specific gravity; 0.884, pour point: less than $-35°$ C., sulfur content; 2.7 wt%, carbon residue: 8.0 wt%, and nitrogen content 0.22 wt%. After materials and components floating on the surface—which had separated from the walls—were removed by suction, a cultivating liquid of the bacteria (FERM BP-63) according to the present invention incubated in a culture medium composed of brine+crude petroleum for 48 hours at 18° C.) was added in an amount of 1/3000 based on the weight of the brine. After 120 hours from the addition of the bacteria, the walls and the bottom of the drum were clean.

FERM BP-63 and 64 in the present invention are deposition numbers of bacteria prepared from FRI Nos. 2927 and 2928 by an incubating method described in this specification. The biological properties of these bacteria of the present invention in the case of incubaton on a conventional culture medium are not different from those of FERM P-2927 and 2928, but a colony after incubation for 48 hours on a culture medium consisting of 0.5 g of crude petroleum, 1 liter of the brine and agar is white and opaque and has a diameter of 1.5 mm.

While the invention has been described in detail and with reference to specific embodiments thereof, it will be apparent to one skilled in the art that various changes and modifications can be made therein without departing from the spirit and scope thereof.

What is claim is:

1. A biologically pure culture of a Pseudomonas bacterium having all the identifying characteristics of Ferm BP-63, BP-64 or a mixture of BP-63 and BP-64 which exhibits an accelerated growth when hydrocarbons are added during a logarithmic growth phase of a growth curve which is generated during cultivation of the bacterium in a Stephanson Wetham trophic culture medium, and which emulsifies a hydrocarbon and brine solution so that the solution becomes nearly transparent through a cloudy state by emulsification and wherein the bacteria perishes after conclusion of assimilation of said hydrocarbons within about the period required for multiplication.

2. A biologically pure culture of a Pseudomonas bacterium of claim 1, wherein said bacterium exhibits a growth stimulation angle of at least 1°.

3. A biologically pure culture of a Pseudomonas bacterium of claim 1, wherein said bacterium possesses an EP-value of at least 0.1.

4. A biologically pure culture of a Pseudomonas bacterium of claim 1, wherein said hydrocarbons are selected from the group consisting of crude petroleum, refined petroleum products, natural gas, and liquid coal.

5. A bacterial preparation for purifying hydrocarbon pollution comprising the biologically pure culture of claim 1, and a coating agent comprising hydrocarbon.

6. A process for purifying a hydrocarbon polluted brine solution area which comprises multiplying in the polluted area said biologically pure culture of a Pseudomonas bacterium of claim 1.

7. A process according to claim 6, wherein the hydrocarbon polluted area is a hydrocarbon polluted sea zone.

8. A process according to claim 6, wherein the hydrocarbon polluted area is an oil tanker, a petroleum storage tank, or an activated sludge processing plant.

9. A process for producing a Pseudomonas bacterium comprising:
(1) subculturing a naturally-occurring Pseudomonas bacterium in a medium comprising hydrocarbons, a nitrogen compound, and brine to obtain a first non-naturally-occurring Pseudomonas bacterium;

(2) subculturing said first non-naturally-occurring Pseudomonas bacterium in a medium comprising hydrocarbons, vitamins, and brine to obtain a second non-naturally-occurring Pseudomonas bacterium;

(3) subculturing the second non-naturally-occurring Pseudomonas bacterium in a medium comprising hydrocarbons and brine to obtain a Pseudomonas bacterium having all the identifing characteristics of FERM BP-63 or BP-64 which exhibits an accelerated growth when hydrocarbons are added during a logarithmic growth phase of a growth curve which is generated during cultivation of the bacterium in a Stephanson Wetham trophic culture medium, and which emulsifies a hydrocarbon and brine solution so that the solution becomes nearly transparent through a cloudy state by emulsification and wherein the process is carried out in the absence of added surfactant; and (4) recovering a Psendomonas bacterium having all the identifing characteristics of FERM BP-63 or BP-64.

10. A process for producing a Pseudomonas bacterium of claim 9, wherein said naturally occurring Pseudomonas bacterium is Fermentation Research Institute Deposit Number FERM P-2927 or FERM P-2928.

11. The process according to claim 9 further comprising:

after Step (3) and before Step (4) acclimatizing the bacterium obtained in Step (3) to a higher concentration of hydrocarbons.

12. The process according to claim 11 further comprising:

after acclimatizing the bacterium and before Step (4), cultivating the bacterium obtained in the acclimatizing Step on a medium comprising hydrocarbons and brine under a particular temperature so that the bacterium exhibits an assimilating ability to a desired temperature range.

13. A biologically pure culture of a Pseudomonas bacterium having all the identifying characteristics of FERM BP-63, BP-64, or a mixture of BP-63 and BP-64 wherein said bacterium is obtained by a process comprising:

(1) subculturing a naturally occurring Pseudomonas bacterium in a medium comprising hydrocarbons, a nitrogen compound, and brine to obtain a first non-naturally-occurring Pseudomonas bacterium;

(2) subculturing said first non-naturally-occurring Pseudomonas bacterium in a medium comprising hydrocarbons, vitamins, and brine to obtain a second non-naturally-occurring Pseudomonas bacterium; and (3) subculturing said second non-naturally-occurring Pseudmonas bacterium in a medium comprising hydrocarbons and brine to obtain a Pseudmonas bacterium which exhibits an accelerated growth during a logarithmic growth phase of a growth curve which is generated during cultivation of the bacterium in a Stephanson Wetham trophic culture medium, and which emulsifies a hydrocarbon and brine solution so that the solution becomes nearly transparent through a cloudy state by emulsification and wherein the bacteria perishes after conclusion of assimilation of said hydrocarbons within about the period required for multiplication.

14. A Pseudomonas bacterium according to claim 13, wherein said bacterium is obtained by a process further comprising:

(4) acclimatizing the bacterium obtained in step (3) to a higher concentration of hydrocarbons.

15. A Pseudomonas bacterium according to claim 14, wherein said bacterium is obtained by a process further comprising:

(5) cultivating the bacterium obtained in step (4) on a medium comprising hydrocarbons and brine under a particular temperature so that the bacterium exhibits an assimilating ability to a desired temperature range.

16. A bacterial preparation for purifying a hydrocarbon polluted brine solution comprising the biologically pure culture of claim 13 and a coating agent comprising a hydrocarbon.

* * * * *